(12) United States Patent
Murata et al.

(10) Patent No.: US 10,449,124 B2
(45) Date of Patent: Oct. 22, 2019

(54) POLYMERIZABLE COMPOSITION FOR DENTAL USE

(71) Applicant: GC Corporation, Tokyo (JP)

(72) Inventors: Takayuki Murata, Tokyo (JP); Nobuhito Takagi, Tokyo (JP); Takayuki Ueno, Tokyo (JP)

(73) Assignee: GC Corporation, Tokyo (JP)

( * ) Notice: Subject to any disclaimer, the term of this patent is extended or adjusted under 35 U.S.C. 154(b) by 33 days.

(21) Appl. No.: 15/749,193

(22) PCT Filed: Jun. 29, 2016

(86) PCT No.: PCT/JP2016/069317
§ 371 (c)(1),
(2) Date: Jan. 31, 2018

(87) PCT Pub. No.: WO2017/026187
PCT Pub. Date: Feb. 16, 2017

(65) Prior Publication Data
US 2018/0221251 A1    Aug. 9, 2018

(30) Foreign Application Priority Data
Aug. 11, 2015    (JP) .................... 2015-158918

(51) Int. Cl.
*A61K 6/083* (2006.01)
*A61K 6/00* (2006.01)
*C08L 47/00* (2006.01)
*C08F 20/10* (2006.01)

(52) U.S. Cl.
CPC ............... *A61K 6/083* (2013.01); *A61K 6/00* (2013.01); *C08F 20/10* (2013.01); *C08L 47/00* (2013.01)

(58) Field of Classification Search
CPC .................................................. A61K 6/083
See application file for complete search history.

(56) References Cited

U.S. PATENT DOCUMENTS

| | | | |
|---|---|---|---|
| 5,145,374 A | 9/1992 | Stansbury | |
| 8,497,332 B2 * | 7/2013 | Kaneko | C08F 220/40 526/224 |
| 2005/0215660 A1 | 9/2005 | Tomikawa et al. | |
| 2008/0242756 A1 | 10/2008 | Kosaka et al. | |
| 2011/0046261 A1 | 2/2011 | Kuboe et al. | |
| 2011/0263805 A1 | 10/2011 | Kaneko | |
| 2012/0016095 A1 | 1/2012 | Saito et al. | |
| 2012/0214900 A1 | 8/2012 | Klee et al. | |

FOREIGN PATENT DOCUMENTS

| | | |
|---|---|---|
| JP | 2008-247801 | 10/2008 |
| JP | 2012-171885 | 9/2012 |
| JP | 2013-509364 | 3/2013 |
| JP | 2014-040585 | 3/2014 |
| JP | 2015-067543 | 4/2015 |
| WO | 2003/082931 | 10/2003 |
| WO | 2009/133912 | 11/2009 |
| WO | 2010/074289 | 7/2010 |

OTHER PUBLICATIONS

Database WPI Week 201420 Thomson Scientific, London, GB; AN 2014-E11957 XP002787651.
Stansbury J W: "Cyclopolymerizable Monomers for Use in Dental Resin Composites", Journal of Dental Research, International Association for Dental Research, US, vol. 69, No. 3, Mar. 1, 1990, pp. 844-848, XP000562158, ISSN: 0022-0345.
J. W. Stansbury, "Cyclopolymerizable Monomers for Use in Dental Resin Composites" Journal of Dental Research, Mar. 1990, vol. 69, No. 3, pp. 844-848, ISSN 0022-0345.
J. W. Stansbury, "Difunctional and Multifunctional Monomers Capable of Cyclopolymerization", Macromolecules, Apr. 1, 1991, vol. 24, No. 8, pp. 2029-2035, ISSN 0024-9297.
International Search Report for PCT/JP2016/069317 dated Sep. 6, 2016.

\* cited by examiner

*Primary Examiner* — Michael F Pepitone
(74) *Attorney, Agent, or Firm* — IPUSA, PLLC

(57) ABSTRACT

A polymerizable composition for dental use including a (meth)acrylate monomer that is able to cyclopolymerize is provided.

4 Claims, No Drawings

POLYMERIZABLE COMPOSITION FOR DENTAL USE

CROSS-REFERENCE TO RELATED APPLICATIONS

This application is a national stage filing under 35 U.S.C. 371 of International Patent Application No. PCT/JP2016/069317, filed Jun. 29, 2016, which claims priority to Japanese Patent Application No. 2015-158918, filed Aug. 11, 2015.

TECHNICAL FIELD

The present invention relates to a polymerizable composition for dental use.

BACKGROUND ART

Conventionally, polymerizable compositions for dental use are used as fillers to fill lost portions of teeth or cavities formed for treatment or as adhesive agents used in repairing teeth.

Before being hardened, polymerizable compositions for dental use are usually in a paste state and arranged to fill a predetermined location such as lost portions within a mouth. Then, after the arrangement and filling, the polymerizable compositions for dental use are hardened to repair lost portions of teeth or the like.

Hence, before being hardened, polymerizable compositions for dental use are required to have an appropriate viscosity and excellent operability so as to be easily arranged to fill lost portions of teeth or the like. Then, after being hardened, polymerizable compositions for dental use are required to have a sufficient mechanical strength such that natural teeth can be replaced with the polymerizable compositions, for example.

In this way, conventionally, various considerations are performed for polymerizable compositions for dental use to have excellent operability before being hardened and to have a sufficient mechanical strength after being hardened.

For example, Patent Document 1 discloses a dental composition that contains a polymerizable monomer component (A) and an amorphous filler (B) having an average particle diameter of 1 μm to 20 μm. The amorphous filler contains silica-based fine particles and coatings of an oxide that covers the surfaces of the silica-based fine particles. The oxide contains a zirconium atom, a silicon atom and an oxygen atom. The dental composition contains 20 to 500 parts by weight of the filler (B) per 100 parts by weight of the polymerizable monomer component (A), and has a viscosity within a range of 10 to 800 Pa·s.

PRIOR ART DOCUMENT

Patent Document

[Patent Document 1] International Publication No. WO 2009/133912

SUMMARY OF THE INVENTION

Problems to be Solved by the Invention

However, in the polymerizable composition for dental use disclosed in Patent Document 1, the operability before being hardened and the mechanical strength after being hardened are not sufficient.

The present invention has been made in view of the problem of the above described conventional art, and one aspect of the present invention has an object to provide a polymerizable composition for dental use that has an excellent operability before being hardened and has an excellent mechanical strength after being hardened.

Means for Solving the Problems

According to one aspect of the present invention, a polymerizable composition for dental use including a (meth)acrylate monomer that is able to cyclopolymerize is provided.

Effects of the Invention

According to one aspect of the present invention, it is possible to provide a polymerizable composition for dental use that has an excellent operability before being hardened and has an excellent mechanical strength after being hardened.

EMBODIMENT OF THE INVENTION

In the following, an embodiment for implementing the present invention will be described. The present invention is not limited to the embodiment described below, and various modifications and substitutions may be made for the embodiment described below without departing from the scope of the present invention.

A configuration example of a polymerizable composition for dental use according to the embodiment will be described.

The polymerizable composition for dental use according to the embodiment may include a (meth)acrylate monomer that is able to cyclopolymerize.

As described above, a polymerizable composition for dental use is required to have an excellent operability before being hardened and to have a sufficient mechanical strength after being hardened. Hence, the inventors of the present invention have earnestly investigated a polymerizable composition for dental use having such characteristics. Then, the inventors have found that a polymerizable composition for dental use containing a (meth)acrylate monomer that is able to cyclopolymerize has an appropriate fluidity in a paste state before being hardened and has a sufficient mechanical strength after being hardened and accomplished the present invention.

According to the investigation by the inventors of the present invention, the polymerizable composition for dental use containing the (meth)acrylate monomer that is able to cyclopolymerize can be a paste having an appropriate fluidity and preventing an increase of viscosity because of not being cyclopolymerized before being hardened. Then, a ring structure is formed at a main chain by a reaction of cyclopolymerization at the time of hardening. Thereby, due to the ring structure, it is possible to develop a high mechanical strength.

Hence, the polymerizable composition for dental use according to the embodiment has characteristics of having an excellent operability before being hardened and of having a high mechanical strength after being hardened.

A specific structure of the (meth)acrylate monomer that is able to cyclopolymerize included in the polymerizable composition for dental use according to the embodiment is not limited particularly. This is because any (meth)acrylate monomer that is able to cyclopolymerize can, without depending on its specific structure, have an appropriate fluidity because a ring structure is not formed before being hardened, and have an enhanced mechanical strength because a ring structure is formed after being hardened. Note that the (meth)acrylate monomer that is able to cyclopolymerize included in the polymerizable composition for dental use according to the embodiment is not limited to one kind and is able to simultaneously include a plurality of kinds having differing structures.

For example, the polymerizable composition for dental use according to the embodiment may include, as the (meth)acrylate monomer that is able to cyclopolymerize, a 1,6-diene-2-carboxylic acid (ester) monomer, and/or a 1,5-diene-2-carboxylic acid (ester) monomer.

Note that in the polymerizable composition for dental use according to the embodiment, the (meth)acrylate monomer that is able to cyclopolymerize may be constituted from a 1,6-diene-2-carboxylic acid (ester) monomer, and/or a 1,5-diene-2-carboxylic acid (ester) monomer.

It is possible to use, as the 1,6-diene-2-carboxylic acid (ester) monomer, a monomer, in which an organic group including a characteristic group of a carboxylic acid (ester) is bonded to an atom at the position 2 of a 1,6-diene monomer, that does not have a substituent group for double bond atoms other than the position 2.

Further, it is possible to use, as the 1,5-diene-2-carboxylic acid (ester) monomer, a monomer, in which an organic group including a characteristic group of a carboxylic acid (ester) is bonded to an atom at the position 2 of a 1,5-diene monomer, that does not have a substituent group for double-bond atoms other than the position 2.

The double-bond character of the 1,6-diene-2-carboxylic acid (ester) monomer and the 1,5-diene-2-carboxylic acid (ester) monomer becomes a conjugated character due to a carboxylic ester group at the position 2. Hence, due to a high polymerization activity and having a carboxylic ester group only at the position 2, it is possible to suppress gelation even when polymerization is performed under a high monomer concentration, and to increase the polymerization speed.

As the 1,6-diene-2-carboxylic acid (ester) monomer, a monomer having a structure expressed by the following formula (a) may be preferably used, for example. Further, As the 1,5-diene-2-carboxylic acid (ester) monomer, a monomer having a structure expressed by the following formula (b) may be preferably used, for example.

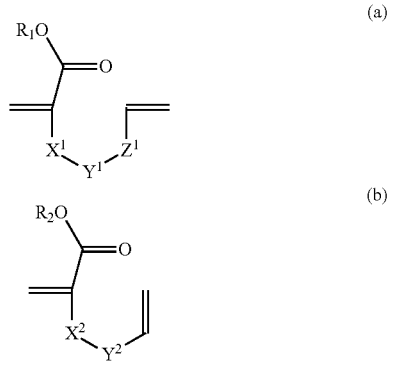

In the above general formulas (a) and (b), $R_1$ and $R_2$ may be a hydrogen atom or a hydrocarbon group having 1 to 20 carbon atoms. The hydrocarbon group here may include a hydrocarbon group a part of which is substituted by a halogen atom or the like.

In a case where the polymerizable composition for dental use according to the embodiment simultaneously includes a 1,6-diene-2-carboxylic acid (ester) monomer and a 1,5-diene-2-carboxylic acid (ester) monomer, $R_1$ and $R_2$ in the above formulas (a) and (b) may have the same structure or may have different structures.

Further, each of $X^1$, $Y^1$, $Z^1$, $X^2$, and $Y^2$ in the above formulas (a) and (b) may be any one selected from an alkylene group, an oxygen atom, and an imino group. Note that it is preferable that at least one of $X^1$, $Y^1$, and $Z^1$ is oxygen atom or an imino group. Further, it is preferable that at least one of $X^2$ and $Y^2$ is an oxygen atom or an imino group As the 1,6-diene-2-carboxylic acid (ester) monomer that has the structure represented by the above general formula (a), allyloxymethyl acrylic esters, and 2-(N-allylaminomethyl)acrylic esters can be preferably used, for example.

Specific examples of the allyloxymethyl acrylic esters include methyl α-allyloxymethylacrylate, ethyl α-allyloxymethylacrylate, butyl α-allyloxymethylacrylate, t-butyl α-allyloxymethylacrylate, cyclohexyl α-allyloxymethylacrylate, dicyclopentadienyl α-allyloxymethylacrylate, isobornyl α-allyloxymethylacrylate, adamantyl α-allyloxymethylacrylate, benzyl α-allyloxymethylacrylate, and the like.

Further, examples of the 2-(N-allylaminomethyl)acrylic esters include methyl 2-(N-allyl N-methylaminomethyl) acrylate, methyl 2-(N-allyl N-ethylaminomethyl)acrylate, methyl 2-(N-allyl N-t-butylaminomethyl)acrylate, methyl 2-(N-allyl N-cyclohexylaminomethyl)acrylate, methyl 2-(N-allyl N-phenylaminomethyl)acrylate, and the like.

As the 1,6-diene-2-carboxylic acid (ester) monomer having the structure represented by the above general formula (a), particularly, allyloxymethyl acrylic esters can be more preferably used. As the allyloxymethyl acrylic esters, one or more kinds selected from methyl α-allyloxymethylacrylate, ethyl α-allyloxymethylacrylate, cyclohexyl α-allyloxymethylacrylate, and benzyl α-allyloxymethylacrylate can be further more preferably used, and methyl α-allyloxymethylacrylate (AMA) can be particularly preferably used.

Further, as the 1,5-diene-2-carboxylic acid (ester) monomer that has the structure represented by the above general formula (b), vinyloxymethyl acrylic esters, N-methyl-N-vinyl-2-(methoxycarbonyl)allylamines, and 2-(N-vinylaminomethyl)acrylic esters can be preferably used, for example.

Specific examples of the vinyloxymethyl acrylic esters include methyl α-vinyloxymethylacrylate, ethyl α-vinyloxymethylacrylate, butyl α-vinyloxymethylacrylate, t-butyl α-vinyloxymethylacrylate, cyclohexyl vinyloxymethylacrylate, dicyclopentadienyl α-vinyloxymethylacrylate, isobornyl α-vinyloxymethylacrylate, adamantyl α-vinyloxymethylacrylate, benzyl α-vinyloxymethylacrylate, and the like.

Further, examples of the N-methyl-N-vinyl-2-(methoxycarbonyl) allylamines include N-methyl-N-vinyl-2-(methoxycarbonyl)allylamine, N-ethyl-N-vinyl-2-(methoxycarbonyl) allylamine, N-t-butyl-N-vinyl-2-(methoxycarbonyl) allylamine, N-cyclohexyl-(methoxycarbonyl) allylamine, N-phenyl-N-vinyl-2-(methoxycarbonyl)allylamine, and the like.

Further, examples of the 2-(N-vinylaminomethyl)acrylic esters include methyl 2-(N-vinyl N-methylaminomethyl) acrylate, methyl 2-(N-vinyl N-ethylaminomethyl)acrylate, methyl 2-(N-vinyl N-t-butylaminomethyl)acrylate, methyl 2-(N-vinyl N-cyclohexylaminomethyl)acrylate, methyl 2-(N-vinyl N-phenylaminomethyl)acrylate, and the like.

As the 1,5-diene-2-carboxylic acid (ester) monomer having the structure represented by the above general formula (b), particularly, methyl α-vinyloxymethylacrylate, ethyl α-vinyloxymethylacrylate, cyclohexyl α-vinyloxymethylacrylate, and benzyl α-vinyloxymethylacrylate can be more preferably used, and methyl α-vinyloxymethylacrylate can be further more preferably used.

In particular, it is more preferable that the polymerizable composition for dental use according to the embodiment contains, as the (meth)acrylate monomer that is able to cyclopolymerize, a 1,6-diene-2-carboxylic acid (ester) monomer having a structure represented by the above general formula (a). Then, as the 1,6-diene-2-carboxylic acid (ester) monomer, allyloxymethyl acrylic esters can be more preferably used as described above. Hence, it is particularly preferable that the polymerizable composition for dental use according to the embodiment contains, as the (meth)acrylate monomer that is able to cyclopolymerize, a monomer having a structure expressed by the following formula (a').

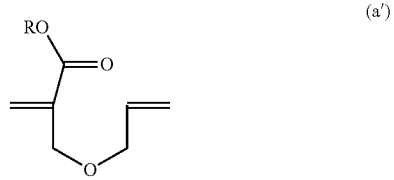
(a')

In the formula (a'), R may be a hydrogen atom or a hydrocarbon group having 1 to 20 carbon atoms. Note that the hydrocarbon group here may include a hydrocarbon group a part of which is substituted by a halogen atom or the like.

The contained amount of a (meth)acrylate monomer that is able to cyclopolymerize included in the polymerizable composition for dental use according to the embodiment is not particularly limited. For example, the contained amount of the (meth)acrylate monomer that is able to cyclopolymerize included in the polymerizable composition for dental use according to the embodiment is preferably in a range of from 5% by weight or more to 60% by weight or less and is more preferably in a range of from 10% by weight or more to 55% or less.

Although a (meth)acrylate monomer that is able to cyclopolymerize included in the polymerizable composition for dental use according to the embodiment has been described above, the (meth)acrylate monomer that is able to cyclopolymerize can form a ring structure in its structure by making a polymerization reaction. This will be described in the following.

A 1,6-diene-2-carboxylic acid (ester) monomer that has a structure represented by the above general formula (a) can form, through cyclopolymerization, a structural unit represented by the following general formula (A1) and/or the general formula (A2).

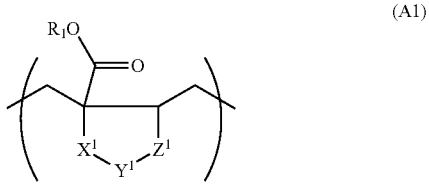
(A1)

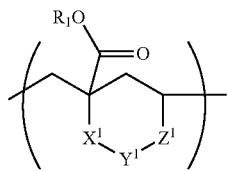
(A2)

Further, a 1,5-diene-2-carboxylic acid (ester) monomer that has a structure represented by the above general formula (b) can form, through cyclopolymerization, a structural unit represented by the following general formula (B1) and/or the general formula (B2).

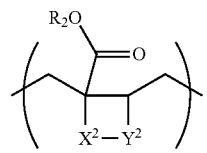
(B1)

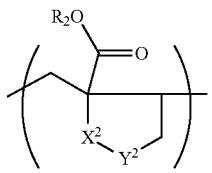
(B2)

A (meth)acrylate monomer that is able to cyclopolymerize included in the polymerizable composition for dental use according to the embodiment can form, through cyclopolymerization, a ring structure therein as represented by the general formulas (A1), (A2), (B1), and (B2), for example. In this way, by forming a ring structure therein at the time of hardening, the mechanical strength of the hardened polymerizable composition for dental use can be enhanced.

The polymerizable composition for dental use according to the embodiment may contain suitable constituents as needed other than a (meth)acrylate monomer that is able to cyclopolymerize.

In the following, examples of the suitable constituents will be described.

The polymerizable composition for dental use according to the embodiment may further contain a (meth)acrylate compound other than an above described (meth)acrylate monomer that is able to cyclopolymerize. Here, the (meth)acrylate compound, other than the above described (meth)acrylate monomer that is able to cyclopolymerize, refers to various kinds of monomers, oligomers and prepolymers of acrylates or methacrylate.

Specific examples of the (meth)acrylate compound, other than a (meth)acrylate monomer that is able to cyclopolymerize, usable in the polymerizable composition for dental use according to the embodiment include methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-methoxyethyl (meth)acrylate, 2-ethylhexyl (meth)acrylate, benzyl (meth)acrylate, 2-hydroxy-1,3-di(meth)acryloxy propane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, pentaerythritol tri(meth)acrylate, trimethylolmethane tri(meth)acrylate, pentaerythritol tetra(meth)acrylate, polybutylene glycol di(meth)acrylate, bisphenol A diglycidyl (meth)acrylate, and the like. A monomer, oligomer, or premolymer of these can be preferably used.

Further, in the polymerizable composition for dental use according to the embodiment, a (meth)acrylate having a urethane bond can be used as the (meth)acrylate compound other than a (meth)acrylate monomer that is able to cyclopolymerize. Examples of the (meth)acrylate having a urethane bond include di-2-(meth)acryloxyethyl-2,2,4-trimethylhexamethylene dicarbamate, 1,3,5-tris[1,3-bis{(meth)acryloyloxy}-2-propoxycarbonylaminohexane]-1,3,5-(1H,3H,5H) triazine-2,4,6-trione, 2,2-bis-4-(3-(meth)acryloxy-2-hydroxypropyl)-phenylpropane, and the like. In addition, examples of the (meth)acrylate having a urethane bond include a (meth)acrylate of a urethane oligomer including 2,2'-di(4-hydroxycyclohexyl) propane, 2-oxypanone, hexamethylene diisocyanate, and 2-hydroxyethyl (meth)acrylate, and a (meth)acrylate of a urethane oligomer including 1,3-butanediol, hexamethylene diisocyanate, and 2-hydroxyethyl (meth)acrylate, and the like. One of these can be used alone or two or more kinds of these can be mixed and used.

In the polymerizable composition for dental use according to the embodiment, as a (meth)acrylate compound, other than a (meth)acrylate monomer that is able to cyclopolymerize, a (meth)acrylate compound having an acid group can be used. A (meth)acrylate compound having an acid group imparts, to the polymerizable composition for dental use according to the embodiment, an adhesive property with respect to a tooth, dental restorative materials that are ceramics such as zirconia and alumina, and an alloy including noble metals.

The (meth)acrylate compound having an acid group is preferably a (meth)acrylate compound having a phosphate group or a carboxyl group. Thus, a (meth)acrylate compound having one or plural phosphate groups or carboxyl groups in one molecule can be used.

Because the phosphate group has acidity stronger than that of the carboxyl group, the phosphate group has higher effect for dissolving a smear layer of a tooth surface and for tooth demineralization. Particularly, the phosphate group can significantly improve an adhesive property with respect to enamel. Examples of a (meth)acrylate compound having a phosphate group include 2-(meth)acryloyloxyethyldihydrogen phosphate, bis[2-(meth)acryloyloxyethyl]hydrogen phosphate, 2-(meth)acryloyloxyethylphenylhydrogen phosphate, 6-(meth)acryloyloxyhexyldihydrogen phosphate, 6-(meth)acryloyloxyhexylphenylhydrogen phosphate, 10-(meth)acryloyloxydecyldihydrogen phosphate, 1,3-di(meth)acryloylpropane-2-dihydrogen phosphate, 1,3-di(meth)acryloylpropane-2-phenylhydrogen phosphate, bis[5-{2-(meth)acryloyloxyethoxycarbonyl}heptyl]hydrogen phosphate, and the like. Particularly, 10-(meth)acryloyloxydecyl dihydrogen phosphate is preferable because of having an excellent adhesive property and stability of the (meth)acrylate compound itself. One of these (meth)acrylate compounds having a phosphate group can be used alone or two or more kinds of these (meth)acrylate compounds having a phosphate group can be mixed and used. Examples of a (meth)acrylate compound having a carboxyl group include 4-(meth)acryloxyethyltrimellitic acid, 4-(meth)acryloxyethyltrimellitic anhydride, 4-(meth)acryloxydecyltrimellitic acid, 4-(meth)acryloxydecyltrimellitic anhydride, 11-(meth)acryloyloxy-1,1-undecanedicarboxylic acid, 1,4-di(meth)acryloyloxypyromellitic acid, 2-(meth)acryloyloxyethylmaleic acid, 2-(meth)acryloyloxyethylphthalic acid, 2-(meth)acryloyloxyethylhexahydrophthalic acid, and the like. Particularly, 4-(meth)acryloxyethyl trimellitic acid and 4-(meth)acryloxyethyl trimellitic acid anhydride are preferable in that these have an excellent adhesive property.

For example, the total amount, contained in the polymerizable composition for dental use according to the embodiment, of a (meth)acrylate monomer that is able to cyclopolymerize and a (meth)acrylate compound other than the (meth)acrylate monomer that is able to cyclopolymerize is not particularly limited, is preferably in a range of from 5% by weight or more to 90% by weight or less, and is more preferably in a range of from 30% by weight or more to 70% or less.

The polymerizable composition for dental use according to the embodiment may further contain a filler. By containing a filler, the mechanical strength when the polymerizable composition for dental use is hardened can be further enhanced.

In a case where a filler is added to a conventional polymerizable composition for dental use, the viscosity of the polymerizable composition for dental use before being hardened becomes high and the operability may be decreased. However, in the polymerizable composition for dental use according to the embodiment, because a (meth)acrylate monomer that is able to cyclopolymerize is used, the viscosity of the polymerizable composition for dental use before being hardened can be maintained in an appropriate range even when a filler is added. Therefore, it is possible to prevent the operability from being decreased.

Kinds of the filler used in the polymerizable composition for dental use according to the embodiment are not limited particularly, and for example, glass such as glass including an alkaline earth metal, such as anhydrous silicic acid, calcium glass, strontium glass, or barium glass, zinc glass, lead glass, alumina glass, potassium glass, or fluoroaluminosilicate glass, powder of synthetic zeolite, phosphate calcium, feldspar, colloidal silica, fumed silica, silicate aluminum, silicate calcium, carbonate magnesium, hydrous silicic acid, hydrous calcium silicate, hydrous aluminum silicate, or quartz may be preferably used.

Note that it is desirable to use these fillers after silanizing the surface by using an organic silicon compound, in order to be bonded to a (meth)acrylate compound included in the polymerizable composition for dental use according to the embodiment.

For example, these fillers may be used after being silanized by using, as a surface treatment agent, an organic silicon compound such as γ-methacryloxypropyltrimethoxysilane, vinyltrichlorosilane, vinyltriethoxysilane, vinyltrimethoxysilane, vinyltriacetoxysilane, or vinyltri(methoxyethoxy)silane.

It is also possible to use, as a filler, an organic-inorganic compound filler that is prepared by mixing and hardening in advance the above described filler with a monomer or an oligomer of a (meth)acrylate compound used in the polymerizable composition for dental use according to the embodiment and thereafter pulverizing the hardened filler. One of these fillers can be used alone or two or more kinds of these fillers can be mixed and used.

In a case where a filler is added to the polymerizable composition for dental use according to the embodiment, the added amount is not particularly limited and can be suitably selected in accordance with a use, a mechanical strength required for the polymerizable composition for dental use, or the like. For example, in the polymerizable composition for dental use, a filler is mixed preferably at a proportion of from 20% by weight or more to 90% by weight or less, and more preferably at a proportion of from 30% by weight or more to 80% by weight or less.

Further, an average particle diameter of the filler is not limited particularly, is preferably in a range of from 0.005 μm or longer to 100 μm or shorter, and is more preferably in a range of from 0.01 μm or longer to 50 μm or shorter. Note that the average particle diameter means a particle diameter at an integrated value 50% in a particle size distribution obtained by a laser diffraction/scattering method.

Further, the polymerizable composition for dental use according to the embodiment may further include a polymerization initiator, for example. A method of initiating polymerization of a (meth)acrylate monomer is not particularly limited, and for example, an energy necessary to initiate polymerization may be supplied, by visible light, an electromagnetic wave (infrared ray, ultraviolet ray, X ray, etc.), an electron beam, to the polymerizable composition for dental use according to the embodiment. Note that without depending on a method of initiate polymerization, by containing a polymerization initiator in the polymerizable composition for dental use according to the embodiment, energy required to initiate polymerization of the (meth) acrylate monomer is greatly reduced and reaction control becomes easy. Hence, it is preferable to contain a polymerization initiator.

It is possible to use, as the polymerization initiator, a peroxide, an azo compound or the like, for example. Specifically, it is possible to use one or more kinds selected from cumene hydroperoxide, diisopropylbenzene hydroperoxide, di-t-butyl peroxide, lauroyl peroxide, benzoyl peroxide, t-butyl peroxy isopropyl carbonate, t-butyl peroxy 2-ethyl hexanoate, azobisisobutyronitrile, 1,1'-azobis(cyclohexanecarbonitrile), 2,2'-azobis(2,4-dimethylvaleronitrile), dimethyl 2,2'-azobis (2-methylpropionate), hydrogen peroxide, persulfate, benzoyl peroxide, or the like. Further, it is also possible to use, in addition to a polymerization initiator, a reductant agent such as amines or a transition metal salt.

Further, the polymerizable composition for dental use according to the embodiment may further include a photopolymerization initiator to give a property of hardening itself. For example, a compound such as an α-diketone-based compound, a ketal-based compound, an anthraquinone-based compound, a thioxanthone-based compound, or a benzoin alkyl-ether compound is effective. Further, an acylphosphine oxide-based compound or the like may be used in combination.

Examples of the α-diketone-based compound include camphorquinone, benzyl, diacetyl, acenaphthenequinone, 9,10-phenanthraquinone, and the like.

Examples of the ketal-based compound include benzyl dimethyl ketal, benzyl diethyl ketal, benzyl di(β-phenylethyl) ketal, benzyl di(2-methoxyethyl) ketal, and the like.

Examples of the anthraquinone-based compound include anthraquinone, β-methylanthraquinone, 1-ethylanthraquinone, and the like.

Examples of the thioxanthone-based compound include 2-ethylthioxanthone, 2-chlorothioxanthone, 2-hydroxy-3-(3, 4-dimethyl-9-oxo-9H-thioxanthen-2-yloxy)-N,N,N-trimethyl-1-propanaminium chloride.

Examples of the benzoin alkyl ether-based compound include benzoin methyl ether, benzoin ethyl ether, benzoin propyl ether, and the like.

Among these photopolymerization initiators, camphorquinone and benzyl can be particularly preferably used.

Further, examples of the acylphosphine oxide-based compound include 2,4,6-trimethylbenzoyldiphenylphosphine oxide, 2,6-dimethylbenzoyldiphenylphosphine oxide, 2,6-dimethoxybenzoyldiphenylphosphine oxide, and the like.

Further, the polymerizable composition for dental use according to the embodiment may contain a thickening agent, for example. By adding a thickening agent, the viscosity of the polymerizable composition for dental use before being hardened can be adjusted as appropriate in accordance with a use and the operability can be especially enhanced.

As the thickening agent, either an inorganic thickening agent or an organic thickening agent may be used. One of these thickening agents can be used alone or two or more kinds of these thickening agents can be mixed and used.

Examples of the inorganic thickening agent include fumed silica, zirconia, silica alumina, alumina, glass, titania, calcium carbonate, kaolin, clay, mica, aluminum sulfate, barium sulfate, calcium sulfate, titanium oxide, calcium phosphate, and the like.

Further, examples of the organic thickening agent include carboxymethyl cellulose calcium, carboxymethyl cellulose sodium, starch, sodium starch glycolate, sodium starch phosphate ester, methyl cellulose, sodium polyacrylate, alginic acid, sodium alginate, propylene glycol alginate ester, casein, casein sodium, polyethylene glycol, ethyl cellulose, hydroxyethyl cellulose, gluten, locust bean gum, gelatin, and the like.

The additive amount of the thickening agent is not limited particularly but can be suitably selected such that the polymerizable composition for dental use according to the embodiment has a desired viscosity in accordance with a use or the like.

To the polymerizable composition for dental use according to the embodiment, an agent such as a polymerization inhibitor, an antioxidant, a discoloration inhibitor, an ultraviolet ray absorber, a surfactant, a pigment, a perfume, or an antibacterial agent may be further added.

According to the polymerizable composition for dental use of the embodiment, it is possible to provide a polymerizable composition for dental use that has an excellent operability before being hardened and has an excellent mechanical strength after being hardened.

Here, consistency may be an index of an operability of the polymerizable composition for dental use.

A specific testing method of the consistency will be described in details with reference to examples.

For example, after a predetermined amount of a polymerizable composition for dental use is arranged between cellophane, a weight is placed on the cellophane via a plate shaped member. The plated shaped member and the weight are removed after an elapse of a predetermined time, and then an average value of lengths of a long side and a short side of the spread polymerizable composition for dental use can be obtained as the consistency.

The consistency of the polymerizable composition for dental use according to the embodiment is preferably greater than or equal to 50 mm and less than or equal to 100 mm, and is more preferably greater than or equal to 60 mm and less than or equal to 100 mm.

As can been seen from the outline of the above described testing method, the consistency is a value obtained by digitizing the degree of spread of the polymerizable composition for dental use for when force is applied to the polymerizable composition for dental use. Then, in a case where the consistency is greater than or equal to 50 mm and less than or equal to 100 mm, the polymerizable composition for dental use is preferable because of being a polymerizable composition for dental use having an appropriate viscosity and fluidity and having an excellent operability.

Further, a specific testing method of the mechanical strength of the polymerizable composition for dental use after being hardened will be described in details with reference to examples, and the mechanical strength of the polymerizable composition for dental use after being hardened can be evaluated by a three point bending test.

The mechanical strength of the polymerizable composition for dental use according to the embodiment after being hardened is preferably greater than or equal to 180 MPa and less than or equal to 350 MPa, and is more preferably greater than or equal to 190 MPa and less than or equal to 350 MPa.

This is because, in a case where the mechanical strength of the polymerizable composition for dental use after being hardened is greater than or equal to 180 MPa, the mechanical strength is sufficient in comparison with natural teeth and the mechanical strength is sufficient such that natural teeth can be replaced with the polymerizable composition for dental use. However, because the mechanical strength is not required to be excessively high, the mechanical strength is preferably less than or equal to 350 MPa as described above.

Although the polymerizable composition for dental use according to the embodiment has been described above, a use of the polymerizable composition for dental use according to the embodiment is not particularly limited. For example, a polymerizable composition for dental use according to the embodiment can be used to fill a lost portion of a tooth or a cavity formed for repair or used as an adhesive agent for fixing in repair. Specifically, for example, a polymerizable composition for dental use according to the embodiment can be used for various uses such as a composite resin, a hard resin, resin cement, a bonding material, an adhesive material for fixing a swinging tooth, a quick curing resin, resin reinforced glass ionomer cement, a core material, a surface coating agent, a temporary crown (TEK) material, a resin block for machining, or a resin block for denture base.

The polymerizable composition for dental use according to the embodiment has an excellent operability before being hardened and has an excellent mechanical strength after being hardened. Hence, the polymerizable composition for dental use can be preferably used for a resin block for machining, for example, because it is easy to fill a mold and the mechanical strength after being hardened is high.

Note that the resin block for machining means a resin block for dental use that is used when a dental prosthesis such as an inlay or a crown is made in a cutting operation by a CAD/CMD apparatus.

A method of producing the resin block for machining will be described. The method of producing the resin block for machining includes following processes:

a process of injecting the polymerizable composition for dental use according to the embodiment into a mold that has a desired shape; and a pressurizing and heating process of pressurizing the mold, into which the polymerizable composition for dental use according to the embodiment has been injected, under a pressure within a range of from 1.0 MPa or more to 8.0 MPa or less and heating at a temperature within a range of from 60° C. or more to 200° C. or less with completion of increasing the pressure.

By applying the above processes, the polymerizable composition for dental use can be polymerized/hardened and molded into a block shape and the resin block for machining can be obtained.

Here, as a material constituting the mold, a material except for metal is preferable, and a synthetic resin is more preferable in terms of its dimensional precision as a mold and moldability. In particular, as a material constituting the mold, a thermoplastic resin or a silicone resin is further more preferable. This is because it becomes possible, by using a material except for metal as the material of the mold, to drastically reduce the occurrence of cracks on a produced mechanical resin block for machining.

Note that in a case where thermoplastic resin is used as a material constituting the block, polyethylene, for example, polypropylene, polyvinyl chloride, polystyrene, polyvinyl acetate, polytetrafluoroethylene, acrylonitrile butadiene styrene resin, acrylic resin, or the like can be preferably used as the thermoplastic resin.

Further, the mold may be a structure such as a porous body. For example, in a case where a synthetic resin is injected into or impregnated into a communicating porous body constituted from ceramics or the like, the polymerizable composition for dental use according to the embodiment can be preferably used as the synthetic resin because the viscosity of a composition before polymerization is low in the polymerizable composition for dental use according to the embodiment.

The shape of the mold is not limited particularly and may have a shape that corresponds to a resin block for machining to be made. The shape of the resin block for machining is not limited particularly and may have a cuboid or a cylinder. Note that it is preferable to make in advance the shape of the resin block for machining close to a shape of an inlay or a crown such that a cut amount in the cutting process can be reduced. Hence, it is also possible to make the shape of the resin block for machining to be made close to a shape of an inlay or the like. In this case, the shape of a mold can be selected in accordance with the shape of the resin block for machining to be made.

Note that for pressure force in the pressurizing and heating process, the pressure force can be set to be greater than or equal to 1.0 MPa so as to sufficiently prevent air bubbles from mixing into the mold and so as to prevent the occurrence of air bubbles that may cause chipping. Further, although the pressure force exceeding 8.0 MPa does not affect the quality of the resin block for dental use itself, the pressure force is preferably less than or equal to 8.0 MPa because it becomes difficult to maintain a high pressure and because further improvements cannot be obtained by increasing the pressure force.

In pressurization in the pressurizing and heating process, the pressurization can be conducted by supplying gas into a heating furnace having a pressure resistance such as an autoclave. At this time, used gas is not particularly limited, an inert gas is preferably used, and nitrogen gas may be preferably used, for example. At this time, before supplying gas into the heating furnace, the inside of the heating furnace is preferably substituted by pressurizing gas in advance.

For a heating temperature in the pressurizing and heating process, the heating temperature can be set to be greater than or equal to 60° C. so as to sufficiently prompt polymerization of a monomer and to prevent a non-polymerized polymer from remaining. Note that it is preferable that the heating temperature is greater than or equal to 80° C. in terms of enhancing productivity and preventing a polymerization time from being lengthened. On the other hand, in a case where the heating temperature exceeds 200° C., a material of packing used for an apparatus such as an autoclave used in heat and pressurization may be limited. Therefore, it is preferable that the heating temperature is less than or equal to 200° C.

A time of conducting the pressurizing and heating process is not particularly limited, and, for example, may be suitably selected in accordance with a size or the like of a resin block for machining to be made. For example, it is preferable that the pressurization and the heating are conducted for 10 minutes or longer and 90 minutes or shorter in total. That is, it is preferable, after increasing the pressure and increasing the temperature to reach a predetermined pressure and temperature, to maintain the predetermined pressure and temperature 10 minutes or longer and 90 minutes or shorter. This is because both the quality and the productivity can be satisfied by conducting the pressurization and the heating for 10 minutes or longer and 90 minutes or shorter.

By producing a resin block for machining under conditions as described above, it is possible to obtain the resin block for machining of which the moldability is excellent and cracks or air bubbles are small. In particular, because the resin block for machining is formed by hardening the polymerizable composition for dental use according to the embodiment, it is possible to obtain the resin block for machining that has an excellent mechanical strength.

The obtained resin block for machining can be made into an inlay or a crown through a cutting process by a NC-controlled processing machine based on three-dimensional data created on the basis of an impression shape collected from the mouth cavity of a patient.

Note that although the resin block for machining is specifically described here for a use example of the polymerizable composition for dental use according to the embodiment, a use of the polymerizable composition for dental use according to the embodiment is not limited to such an embodiment. As described above, the polymerizable composition for dental use according to the embodiment can be used in various uses and can be used in accordance with a usage of the various uses.

EXAMPLES

In the following, specific examples and comparative examples will be described. The present invention is not limited to these examples.

First, an evaluation method of pasty polymerizable compositions for dental use made in the examples and the comparative examples will be described.
(1) Consistency A syringe was filled with a pasty polymerizable composition for dental use made in each of the examples and the comparative examples, and 0.5 ml of the pasty polymerizable composition for dental use was ejected on cellophane.

After cellophane was covered on the ejected polymerizable composition for dental use in a quiet manner, a cover glass and a weight, which had 840 g in total, were placed in a quiet manner and left for 60 seconds. The cover glass and the weight were removed immediately after an elapse of 60 seconds, and lengths of the long side and the short side of the spread paste were measured and an average value of the length of the long side and the length of the short side was obtained as the consistency.
(2) Moldability A syringe was filled with the pasty polymerizable composition for dental use made in each of the examples and the comparative examples, and the pasty polymerizable composition for dental use was injected into a polypropylene mold of 12 mm×14 mm×20 mm.

The mold filled with the polymerizable composition for dental use was fixed in an autoclave (manufactured by KYOSIN ENGINEERING COOPERATION). Then, after nitrogen, whose concentration was 99.9%, was introduced into the autoclave until reaching 0.3 MPa, nitrogen was emitted and substituted in the autoclave. Similarly, nitrogen was substituted in the autoclave three times in total including the above first time substitution such that oxygen concentration was less than 1.0% in the autoclave.

After completing the above described substitution operation, nitrogen, whose concentration was 99.9%, was further supplied into the autoclave to increase the pressure to 1.0 MPa. Simultaneously with the completion of increasing the pressure, the temperature in the furnace was increased to 110° C. to perform hardening/polymerization one hour. After the elapse of one hour, the pressure was decreased to atmospheric pressure. After the furnace cooled down to 60° C. or less, the mold was extracted and the polymerized resin block for dental use was extracted from the mold.

Whether the molded resin block for dental use was along the inner surface shape of the mold without an empty space and the shape was appropriate was checked. Then, when the molded resin block for dental use was along the inner surface shape of the mold without an empty space and the shape was appropriate, it was evaluated as excellent. Further, in a case where an empty space was present, it was evaluated as an empty space was present.
(3) Mechanical Strength The resin block for dental use molded for the evaluation of the moldability was cut into 1.2 mm×4.0 mm×14.0 mm, and after the surface was made uniform by waterproof abrasive paper No. 1000, it was attached to a flexural strength testing apparatus (autograph, manufactured by Shimadzu Corporation). Then, a three-point flexural strength was measured under conditions of 1 mm/min of a crosshead speed and 12 mm of an inter-fulcrum distance, and the measured result was treated as the mechanical strength.

Example 1

Materials were weighed and mixed to prepare a pasty polymerizable composition for dental use whose composition was as illustrated in the table 1.

Specifically, a (meth)acrylate monomer, a filler, and a polymerization initiator were weighed and mixed to prepare the pasty polymerizable composition for dental use.

Note that as the (meth)acrylate monomer, 25% by weight of UDMA (di-2-methacryloxyethyl-2,2,4-trimethylhexamethylene dicarbamate) and 12% by weight of AMA (methyl α-allyloxymethylacrylate) were used.

Further, as the filler, 60% by weight of MPTS 6% by mass processed barium glass was used.

Here, the MPTS means γ-methacryloxypropyltriethoxysilane. Further, the filler of MPTS 6% by mass processed barium glass means a filler obtained by processing barium glass power such that γ-methacryloxypropyltriethoxysilane, which is a silane coupling agent, is at 6% by mass with respect to the barium glass powder.

Further, the average particle diameter of the used filler was 0.4 μm as illustrated in the table 1. Note that the average particle diameter means a particle diameter at an integrated value 50% in a particle size distribution obtained by a laser diffraction/scattering method. Note that, in the table 1, although the average particle diameters are indicated for the fillers other than the filler used in the example 1, similar to the above description, these average particle diameters mean particle diameters at an integrated value 50% in a particle size distribution obtained by a laser diffraction/scattering method.

Further, as the polymerization initiator, 1% by weight of BPO (benzoyl peroxide) was used.

The obtained polymerizable composition for dental use was evaluated by the above described method.

The results are indicated in the table 1.

Example 2 to Example 8

Pasty polymerizable compositions for dental use were prepared and evaluated in a manner similar to the example 1 other than proportions of the mixed materials indicated in the table 1.

The results are indicated in the table 1.

Note that the numerical values for the mixed materials in the table 1 are in % by weight.

Further, the abbreviated names used for the (meth)acrylate monomers in the table 1 respectively mean the following chemical substances.

UDMA: di-2-methacryloxyethyl-2,2,4-trimethylhexamethylene dicarbamate
Bis-GMA: bisphenol A diglycidyl methacrylate
NPG: neopentyl glycol dimethacrylate
3G: triethylene glycol dimethacrylate
AMA: methyl α-allyloxymethylacrylate Among the above described (meth)acrylate monomers, AMA corresponds to a (meth)acrylate monomer that is able to cyclopolymerize.

Further, BPO used as the polymerization initiator indicates benzoyl peroxide.

Furthermore, in the table 1, the organic-inorganic compound filler indicated as the filler means a filler prepared by the following procedure.

UDMA and 3G were mixed at a weight ratio of 1 to 1, and azoisobutyronitrile was further added to prepare a mixed liquid. Note that azoisobutyronitrile was added such that its amount contained in the obtained mixed liquid was 1% by weight.

The obtained mixed liquid and barium glass powder, whose average particle diameter was 2 μm, were mixed at a weight ratio of 1 to 1, and thermally hardened at 110° C. The polymerized substance after being hardened was crushed to obtain the organic-inorganic compound filler having the average diameter 10 μm.

Further, in the table 1, the MPTS 6% by mass processed strontium glass means a filler obtained by processing strontium glass power such that γ-methacryloxypropyltriethoxysilane, which is a silane coupling agent, is at 6% by mass with respect to the strontium glass powder.

Comparative Example 1 to Comparative Example 3

Pasty polymerizable compositions for dental use were prepared and evaluated in a manner similar to the example 1 other than proportions of the mixed materials indicated in the table 1.

The results are indicated in the table 1.

| | | | | EXAMPLE 1 | EXAMPLE 2 | EXAMPLE 3 | EXAMPLE 4 | EXAMPLE 5 | EXAMPLE 6 |
|---|---|---|---|---|---|---|---|---|---|
| MIXED MATERIALS (% BY WEIGHT) | (METH) ACRYLATE MONOMER | | UDMA | 25 | 12 | — | 5 | 10 | 5 |
| | | | Bis-GMA | — | — | 7 | — | — | — |
| | | | NPG | — | — | 5 | — | — | — |
| | | | 3G | — | — | 10 | — | — | — |
| | | | AMA | 12 | 25 | 15 | 27 | 24 | 50 |
| | FILLER | ORGANIC-INORGANIC COMPOUND FILLER | AVERAGE PARTICLE DIAMETER 10 μm | — | — | — | — | 8 | — |
| | | MPTS 6% BY MASS PROCESSED BARIUM GLASS | AVERAGE PARTICLE DIAMETER 0.4 μm | 60 | 60 | 60 | 67 | 55 | 36 |
| | | MPTS 6% BY MASS PROCESSED STRONTIUM GLASS | AVERAGE PARTICLE DIAMETER 0.7 μm | — | — | — | — | — | — |
| | | SILICA FINE POWDER | AVERAGE PARTICLE DIAMETER 0.016 μm | 2 | 2 | 2 | — | 2 | 8 |
| | POLYMERIZATION INITIATOR | | BP0 | 1 | 1 | 1 | 1 | 1 | 1 |
| | EVALUATION | | CONSISTENCY (mm) | 54 | 62 | 59 | 67 | 69 | 88 |
| | | | MOLDABILITY | EXCELLENT | EXCELLENT | EXCELLENT | EXCELLENT | EXCELLENT | EXCELLENT |
| | | | MECHANICAL STRENGTH (MPa) | 231 | 223 | 248 | 221 | 209 | 192 |

| | | | | EXAMPLE 7 | EXAMPLE 8 | COMPARATIVE EXAMPLE 1 | COMPARATIVE EXAMPLE 2 | COMPARATIVE EXAMPLE 3 |
|---|---|---|---|---|---|---|---|---|
| MIXED MATERIALS | (METH) ACRYLATE | | UDMA | 14 | 15 | 12 | 12 | — |
| | | | Bis-GMA | — | — | 25 | — | — |

-continued

| (% BY WEIGHT) | MONOMER | NPG | | — | — | — | 25 | 10 |
|---|---|---|---|---|---|---|---|---|
| | | 3G | | — | — | — | — | 10 |
| | | AMA | | 22 | 16 | — | — | — |
| | FILLER | ORGANIC-INORGANIC COMPOUND FILLER | AVERAGE PARTICLE DIAMETER 10 μm | — | 16 | — | — | — |
| | | MPTS 6% BY MASS PROCESSED BARIUM GLASS | AVERAGE PARTICLE DIAMETER 0.4 μm | 40 | 26 | 62 | 60 | 79 |
| | | MPTS 6% BY MASS PROCESSED STRONTIUM GLASS | AVERAGE PARTICLE DIAMETER 0.7 μm | 21 | 26 | — | — | — |
| | | SILICA FINE POWDER | AVERAGE PARTICLE DIAMETER 0.016 μm | 2 | — | — | 2 | — |
| | POLYMERIZATION INITIATOR | BPO | | 1 | 1 | 1 | 1 | 1 |
| | EVALUATION | CONSISTENCY (mm) | | 53 | 67 | 35 | 55 | 36 |
| | | MOLDABILITY | | EXCELLENT | EXCELLENT | EMPTY SPACE WAS PRESENT | EXCELLENT | EMPTY SPACE WAS PRESENT |
| | | MECHANICAL STRENGTH (MPa) | | 234 | 225 | 226 | 153 | 169 |

In the examples 1 to 8 in which AMA that is able to cyclopolymerize was mixed, the consistency, the moldability, and the mechanical strength were all excellent. That is, it was confirmed that polymerizable compositions for dental use having an excellent operability before being hardened and having an excellent mechanical strength after being hardened were obtained.

On the other hand, in the comparative example 1, the mechanical strength was 226 MPa, which is a preferable value, but the consistency was 35 mm, which is a low value. It was confirmed that the fluidity was low. That is, it was confirmed that the operability before being hardened was inferior. Further, an empty space was confirmed on the surface of the molded resin block for dental use.

Further, in the comparative example 2, the consistency was 55 mm, which is a preferable value, and the moldability was also excellent, but the mechanical strength was 153 MPa, which is a low value. It was confirmed that the mechanical strength after being hardened was inferior.

In the comparative example 3, the consistency and the mechanical strength were low, and an empty space occurred on the surface of the molded block. That is, it was confirmed that the operability before being hardened and the mechanical strength after being hardened were inferior.

It is considered that because a (meth)acrylate monomer that is able to cyclopolymerize was not contained in the comparative examples 1 to 3, it was impossible to obtain a polymerizable composition for dental use that satisfies both an operability before being hardened and a mechanical strength after being hardened.

Although the polymerizable compositions for dental use have been described with reference to the embodiment and the examples, the present invention is not limited to the embodiment and the examples described above. Various modifications and changes may be made within the scope of the present invention as set forth in the claims.

The present international application is based upon and claims the benefit of priority of Japanese Patent Application No. 2015-158918, filed on Aug. 11, 2015, the entire contents of 2015-158918 are hereby incorporated herein by reference.

The invention claimed is:

1. A polymerizable composition for dental use comprising:
   a (meth)acrylate monomer that is able to cyclopolymerize; and
   a filler
   wherein the (meth)acrylate monomer is a 1,6-diene-2-carboxylic acid monomer, a 1,6-diene-2-carboxylic acid ester monomer, a 1,5-diene-2-carboxylic acid monomer, and/or a 1,5-diene-2-carboxylic acid ester monomer,
   wherein a content of the (meth)acrylate monomer is greater than or equal to 5% by mass and less than or equal to 60% by mass,
   wherein an average particle diameter of the filler is greater than or equal to 0.005 μm and less than or equal to 100 μm, the average particle diameter being a particle diameter at an integrated value 50% in a particle size distribution obtained by a laser diffraction/scattering method,
   wherein a content of the filler is greater than or equal to 20% by mass and less than or equal to 90% by mass, and
   wherein the polymerizable composition is in a paste state and has a consistency of greater than or equal to 50 mm and less than or equal to 100 mm.

2. The polymerizable composition for dental use according to claim 1, wherein a monomer having a structure expressed by a following formula (1) is contained as the (meth)acrylate monomer that is able to cyclopolymerize where R is a hydrogen atom or a hydrocarbon group having 1 to 20 carbon atoms:

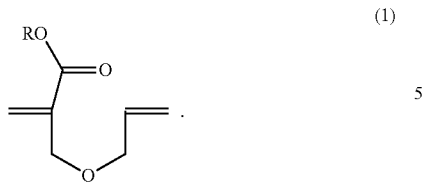

(1)

3. The polymerizable composition for dental use according to claim 1, wherein the mechanical strength of the polymerizable composition after being hardened is greater than or equal to 180 MPa and less than or equal to 350 MPa.

4. The polymerizable composition for dental use according to claim 1, wherein the polymerizable composition is used for producing a resin block.

\* \* \* \* \*